United States Patent
Kircher et al.

(10) Patent No.: US 10,519,482 B2
(45) Date of Patent: Dec. 31, 2019

(54) FORMULATIONS AND PROCESS FOR ISOLATING VIABLE MICROORGANISMS FROM POSITIVE BLOOD CULTURES

(71) Applicant: Becton, Dickinson and Company, Franklin Lakes, NJ (US)

(72) Inventors: Susan M. Kircher, Hanover, PA (US); Vanda White, Baltimore, MD (US); William B. Brasso, Columbia, MD (US); Dyan Luper, Cockeysville, MD (US); James Y. Zhou, Columbia, MD (US); Julie L. Rosales, Randallstown, MD (US); Jeffery H. Bruton, Randallstown, MD (US); John D. Mantlo, Westminster, MD (US); Adrien P. Malick, Sparks, MD (US); Donald R. Callihan, Cockeysville, MD (US); Ben Turng, Tucson, AZ (US); Liping Feng, Baltimore, MD (US); Curtis M. Gosnell, Fallston, MD (US); Patrick Shawn Beaty, Dallastown, PA (US); John P. Douglass, York, PA (US)

(73) Assignee: Becton, Dickinson And Company, Franklin Lakes, NJ (US)

(*) Notice: Subject to any disclaimer, the term of this patent is extended or adjusted under 35 U.S.C. 154(b) by 40 days.

(21) Appl. No.: 14/381,388

(22) PCT Filed: Feb. 28, 2013

(86) PCT No.: PCT/US2013/028249
§ 371 (c)(1),
(2) Date: Aug. 27, 2014

(87) PCT Pub. No.: WO2013/130759
PCT Pub. Date: Sep. 6, 2013

(65) Prior Publication Data
US 2015/0125895 A1    May 7, 2015

Related U.S. Application Data

(60) Provisional application No. 61/604,732, filed on Feb. 29, 2012.

(51) Int. Cl.
| C12Q 1/14 | (2006.01) |
| C12Q 1/24 | (2006.01) |
| C12N 1/02 | (2006.01) |
| C12N 1/20 | (2006.01) |
| C12N 1/04 | (2006.01) |
| C12Q 1/06 | (2006.01) |

(52) U.S. Cl.
CPC .......... *C12Q 1/14* (2013.01); *C12N 1/02* (2013.01); *C12N 1/20* (2013.01); *C12Q 1/24* (2013.01)

(58) Field of Classification Search
None
See application file for complete search history.

(56) References Cited

U.S. PATENT DOCUMENTS

| 5,314,822 A * | 5/1994 | Bailey .............. C12N 1/20 435/252.1 |
| 5,922,593 A | 7/1999 | Livingston |
| 6,096,272 A | 8/2000 | Clark et al. |
| 6,372,485 B1 | 4/2002 | Clark et al. |
| 6,849,422 B1 | 2/2005 | Wiles et al. |
| 7,115,384 B2 | 10/2006 | Clark et al. |
| 7,425,327 B2 | 9/2008 | Masure et al. |
| 8,252,546 B2 | 8/2012 | Briles et al. |
| 2005/0124027 A1 | 6/2005 | Walsh |
| 2006/0127924 A1 * | 6/2006 | Hellyer ............. C12Q 1/689 435/6.12 |
| 2010/0129857 A1 | 5/2010 | Walsh et al. |
| 2010/0129858 A1 | 5/2010 | Walsh et al. |

(Continued)

FOREIGN PATENT DOCUMENTS

| CN | 1781931 A | 6/2006 |
| EP | 0795751 A2 | 9/1997 |

(Continued)

OTHER PUBLICATIONS

Rubins, J.B. et al. Jan. 1995. Dual function of pneumolysin in the early pathogenesis of murine pneumococcal pneumonia. Journal of Clinical Investigation 95: 142-150. specif. pp. 142, 144, 148.*
Hassan-King, M. et al. 1994. Detection of *Streptococcus pneumoniae* DNA in blood cultures by PCR. Journal of Clinical Microbiology 32(7): 1721-1724. specif. p. 1721.*
Holt, L.B. 1962. The culture of *Streptococcus pneumoniae*. Journal of General Microbiology 27: 327-330. specif. pp. 327, 329.*
DeBurger, B. et al. 2008. What's new in the world of swabs? Continuing Education Topics & Issues, Article 332, 0.1 CEC, pp. 18-21 . specif. pp. 18, 20.*

(Continued)

*Primary Examiner* — Renee Claytor
*Assistant Examiner* — Sharon M. Papciak
(74) *Attorney, Agent, or Firm* — Botos Churchill IP Law LLP

(57) ABSTRACT

Various embodiments disclosed herein provide for reagents and methods for rapidly isolating viable microbial cells, including *S. pneumoniae*, from positive blood culture samples. The resulting microbial pellet can be used for both identification and growth-based methods such as antimicrobial susceptibility testing. The buffers described herein may contain a base solution, non-ionic detergents, thiols, and optionally, ammonium chloride. The disclosed methods provide a process for rapidly isolating and concentrating viable microorganism (s) from PBC samples using only one sample preparation tube and centrifugation while removing cellular debris from the mammalian blood cells that may interfere with identification methods.

5 Claims, 2 Drawing Sheets

(56) References Cited

U.S. PATENT DOCUMENTS

2013/0089886 A1    4/2013    Feng et al.

FOREIGN PATENT DOCUMENTS

| WO | 2008084409 A2 | 7/2008 |
|---|---|---|
| WO | 2010100612 A1 | 9/2010 |

OTHER PUBLICATIONS

BD Diagnostics. Columbia Broth. Tryptic Soy Broth. Product catalogue 2009-2010. Dehydrated Culture Media and Ingredients. cat# 294420 and 211822-25. Appended formulation list from Difco & BBL Manual, 2nd edition. specif. renumbered pp. 8 and 12.*

Sun Zhen et al., Rapid Extraction of Genome DNA from Avian Blood, Anhui Agricultural Sciences, vol. 38, No. 16, pp. 8449-8452, 2010.

"The case for accelerated susceptibility testing in the Era of Antibiotic resistance", A White Paper by MicroPhage, Inc., Mar. 30, 2011.

B. M. Charalambous et al: "Quantitative Validation of Media for Transportation and Storage of *Streptococcus pneumoniae*", Journal of Clinical Microbiology, vol. 41, No. 12, Dec. 1, 2003, pp. 5551-5556. XP055062380.

Baker et al.,, "Action of synthetic detergents on the metabolism of bacteria", Oct. 14, 1940.

Bhakdi et al., "Mechanism of membrane damage by streptolysin-O", Infection and Immunity, Jan. 1985, vol. 47, No. 1, p. 52-60.

Bruins et al., "Identification and susceptibility testing of enterobacteriaceae and pseudomonas aeruginosa by Direct Inoculation from Positive BACTEC Blood Culture Bottles into Vitek 2", Journal of Clinical Microbiology, Jan. 2004, vol. 42, No. 1, p. 7-11.

Calbiochem, "Guide for solubilization of membrane proteins and selecting tools for detergent removal", Biological Detergents, 2006.

Chapin et al., "Direct susceptibility testing of positive blood cultures by using sensititre broth microdilution plates", Journal of Clinical Microbiology, Oct. 2003, p. 4751-4754.

Drancourt, "Detection of microorganisms in blood specimens using matrix-assisted laser desorption ionization time-of-flight mass spectrometry: a review", Clin Microbiol Infect, Jun. 8, 2010 (2010), 16: 1620-1625.

Elder et al., "Verification and validation of procedures in the clinical microbiology laboratory", Feb. 1997, Cumulative Techniques and Procedures in Clinical Microbiology, No. 31.

Ferroni et al., "Real-Time identification of bacteria and *Candida* species in positive blood culture broths by Matrix-Assisted laser desorption ionozation-time of flight mass spectrometry", Journal of Clinical Microbiology, May 2010, vol. 48, No. 5, p. 1542-1548.

Funke et al., "Use of the BD Phoenix automated microbiology system for direct identification and susceptibility testing of Gram-Negative rods from positive blood cultures in a Three-Phase trial", Journal of Clinical Microbiology, Apr. 2004, vol. 42, No. 4, p. 1466-1470.

Giudicelli et al., "Attachment of pneumococcal autolysin to wall teichoic acids, an essential step in enzymatic wall degradation", Journal of Bacteriology, 1984, 158(3):1188.

Hansson, "Microfluidic blood sample preparation for rapid sepsis diagnostics", KTH Engineering Sciences, 2012.

Howden R., "Use of anaerobic culture for the improved isolation of *Streptococcus pneumoniae*", J. Clin. Path., 1976, 29, 50-53.

International Search Report for Application No. PCT/US2013/028249 dated May 23, 2013.

Lehtonen, Olli-Pekka J., "Inhibition of pneumococca; autolysis in Lysis-Centrifugation Blood Culture", Journal of Clinical Microbiology, Sep. 1986, vol. 24, No. 3, p. 493-494.

Ling et al., "Evaluation of VITEK 2 rapid identification and susceptibility testing system against Gram-Negative Clinical Isolates", Journal of Clinical Microbiology, Aug. 2001, vol. 39, No. 8, p. 2964-2966.

Lupetti et al., "Rapid identification and antimicrobial susceptibiliity profiling of Gram-positive cocci in blood cultures with the Vitek 2 system", Eur J Clin Microbiol Infect Dis (2010) 29:89-95.

Petti et al., "*Streptococcus pneumoniae* antigen test using positive blood culture bottles as an alternative method to diagnose pneumococcal bacteremia", Jounral of Clinical Microbiology, May 2005, vol. 43, No. 5, p. 2510-2512.

Pirtle et al: "Nitrogen-Containing and Carbohydrate-Containing Antigen From Actinomyces Bovis.", Journal of Bacteriology, vol. 89, Mar. 1, 1965, pp. 880-888. XP055062084.

Prod'hom et al., "Matrix-assisted laser desorption ionization-time of flight mass spectrometry for direct bacterial identification from positive blood culture pellets", Journal of Clinical Microbiology, Apr. 2010, vol. 48, No. 4, p. 1481-1483.

Pulliam et al: "Biochemical properties of C02-dependent streptococci.", Journal of Clinical Microbiology, vol. 12, No. 1, Jul. 1, 1980, pp. 27-31. XP055062102.

Sigma-Aldrich, Inc., Product Information Sheet, Mutanolysin, Product No. M9901, Sep. 2007.

Stevenson et al., "Rapid identification of bacteria in positive blood culture broths by matrix-assisted laser desorption ionization-time of flight mass spectrometry", Journal of Clinical Microbiology, Feb. 2010, vol. 48, No. 2, p. 444-447.

Zierdt, charles H., "Simplified lysed-blood culture technique", Journal of Clinical Microbiology, Mar. 1986, vol. 23, No. 3, p. 452-455.

BacT/Alert® FA Package insert. 9300221 A-2010/10 [retrieved from internet on Sep. 4, 2017]. https://techlib.biomerieux.com/wcm/techlib/techlib/documents/LLUS/Package_Insert/64971001-64972000/Package_Insert_-_9300221_-_A_-_en_-_259791.pdf ***** Category: A.

Zimbro, M., et al., 'Difco and BBL Manual', Becton, Dickinson and Company, 2003, pp. 155 and 558. *****

Kroumova, et al., "Direct identification of bacteria in blood culture by matrix-assisted laser desorption/ionization time-of-flight mass spectrometry: a new methodological approach", Rapid Commun. Mass Spectrom, May 26, 2011, pp. 2247-2249, vol. 25 (wileyonlinelibrary.com) DOI:10.1002/rcm 5113.

Hiroshima-City Medical Association News Letter, No. 527, Appendix, pp. 5-8, Mar. 15, 2010.

Morello, et al., "New Medium for Blood Cultures", Applied Microbiologiy, Jan. 1969, vol. 17 No. 1, pp. 68-70.

Japanese Office Action for Application No. 2014-560029 dated Jan. 10, 2017.

Charalambous, B.M., et al, "Quantitative Validation of Media for Transportation and Storage of *Streptococcus pneumoniae*", Journal of Clinical Microbiology, Dec. 2003, vol. 41 No. 12, American Society of Microbiology.

Holt, L.B., "The Culture of *Streptococcus pneumoniue*", J.gen. Microbiol, The Wright-Fleming Institute, St Mary's Hospital Medical School, London, W. 2,. Sep. 1961, vol. 27, pp. 327-330, Great Britain.

The State Intellectual Property Office of P.R.C. Search Report for CN application No. 2013800210361 dated Feb. 15, 2017.

\* cited by examiner

FORMULATIONS AND PROCESS FOR ISOLATING VIABLE MICROORGANISMS FROM POSITIVE BLOOD CULTURES

CROSS-REFERENCE TO RELATED APPLICATIONS

The present application is a national phase entry under U.S.C. § 371 of International Application No. PCT/US2013/028249 filed Feb. 28, 2013, published in English, which claims the benefit of the filing date of U.S. Provisional Patent Application No. 61/604,732, filed Feb. 29, 2012, the disclosures of which are hereby incorporated herein by reference.

RELATED APPLICATIONS

This application is related in subject matter to U.S. patent application Ser. No. 13/647,072, filed Oct. 8, 2012, which claims the benefit of the filing date of U.S. Provisional Application No. 61/544,407, filed Oct. 7, 2011, the disclosures of which are hereby incorporated herein by reference.

BACKGROUND OF THE INVENTION

Sepsis is a serious medical condition caused by an overwhelming response of the host immune system to infection. It can trigger widespread inflammation, which can give rise to impaired blood flow. As sepsis progresses, the body's organs can be starved for oxygen and nutrients, causing permanent damage and eventual failure. Left improperly diagnosed or otherwise untreated, the heart may weaken and septic shock can occur, leading to multiple organ failure and death. Blood cultures are required to detect the presence of bacteria or yeast in the blood of sepsis patients. If a microorganism is present, (positive blood culture ("PBC")) the microorganism(s) must be identified and antibiotic susceptibility determined in order to provide appropriate treatment. The PBC samples are used to isolate, identify and perform antimicrobial susceptibility testing ("AST"). The microorganism(s) are often identified by methods such as mass spectrometry, including MALDI-TOF/MS or phenotypic growth-based methods, such as Phoenix™ ID.

In order to identify the microorganism(s), perform phenotypic analysis on the microorganism, and perform AST testing, intact, viable microorganism(s) need(s) to be isolated from the blood cells and other material in the collected sample. For identification of the microorganism by mass spectrometry, the microbial sample needs to be sufficiently free from substances known to interfere with MALDI-TOF/MS identification, such as blood cell components, other cellular debris, and salts. In addition, the microbial sample needs to be of sufficient quantity in order to obtain a reliable identification. Phenotypic identification methods, such as Phoenix™ ID, require intact, viable microorganism free from substances that may interfere with the enzymatic substrates of the assay. For AST testing, such as Phoenix™ AST, the microbial sample needs to contain viable, unaltered microorganism capable of growth in the presence of antibiotic, if resistance mechanisms are present, during performance of the assay. It is important for all methods to be of sufficient quantity and purity as carryover of residual blood or media components will interfere either directly or by falsely increasing the concentration (turbidity) of microorganism.

Current techniques for isolating viable microorganism from a PBC sample include sub-culturing the microorganism(s), which can take up to 72 hours. This results in the delay of treatment or treatment with inappropriate antibiotics.

Certain strains of microorganisms are particularly difficult to isolate from a PBC sample while maintaining viability of the organism, such as, for example, Streptococcus pneumoniae (S. pneumoniae). Part of this difficulty is traced to the activation of autolysin by S. pneumoniae which causes the microbial cells to "self-destruct". See "Streptococcus pneumoniae Antigen Test Using Positive Blood Culture Bottles as an Alternative Method To Diagnose Pneumococcal Bacteremia", Journal of Clinical Microbiology, Vol. 43, No. 5, May 2005, p. 2510-2512. The current method for isolating microorganisms from septic patients, including, S. pneumoniae, includes inoculating blood culture bottles. Once a positive signal is achieved, a portion of the PBC sample is removed to perform a gram stain and another portion is used to sub-culture the microorganism. Microbial colonies from the sub-culture are used to perform downstream testing such as identification by MALDI-TOF/MS, phenotypic identification methods, and AST testing.

Additional techniques for isolating viable microorganism(s) from a PBC sample often utilize liquid separation methods containing lysis buffers with detergents that lyse the blood cells in the PBC sample. After lysis, the lysed blood cells can be removed while the microorganism(s) is/are retained. However, the use of these lysis buffers often result in compromised, damaged, or non-viable microorganism(s) which is/are insufficient for performing certain growth-based identification methods such as AST testing.

One such liquid separation method, the Bruker Sepsityper™ system, allows for direct testing of the microorganism from a PBC sample by MALDI-TOF/MS without the need for sub-culturing the microorganism. This method uses Sodium Dodecyl Sulfate ("SDS") and centrifugation to generate a pellet of microbes. While the Sepsityper™ method will generally support MALDI-TOF/MS testing of the microbial pellet, there is insufficient viability to support growth-based identification methods and AST methods, due to the interaction of the harsh detergents on the microbial cell wall.

Prod'hom et al., "Matrix-assisted Laser Desorption Ionization-Time of Flight Mass Spectrometry for Direct Bacterial Identification from Positive Blood Culture Pellets", Journal of Clinical Microbiology, Vol. 48, No. 4, p. 1481-1483 (Feb. 17, 2010). discloses a method for lysing erythrocytes in a PBC sample using ammonium chloride to prepare a bacterial pellet for MALDI-TOF/MS analysis. However, these methods are insufficient in obtaining reliable MALDI-TOF/MS data across a panel of microorganism, including S. pneumoniae. In addition, there is no indication that these methods will maintain sufficient viability of the microorganism for use in growth-based identification methods and AST testing.

Hansson et al., "Microfluidic Blood Sample Preparation for Rapid Sepsis Diagnostics", KTH Engineering Sciences, (2012) suggests the use of detergents for lysing blood cells and selectively lysing certain types of blood cells with ammonium chloride. However, this reference is silent with regard to specific formulations or methods that would allow for the isolation of viable microorganism from a PBC sample that is free from interfering substances and would allow for multiple downstream testing from one PBC sample, such as both MALDI-TOF/MS identification and AST testing.

Both M. Drancourt, "Detection of Microorganisms in Blood Specimens Using Matrix-assisted Laser Desorption Ionization Time-of-flight Mass Spectrometry: A Review, *Clinical Microbiology and Infection,* 16:1620-1625, (2010) and WO 2010/100612 to Nassif et al. describe methods for isolating microorganism from a PBC sample which include removing red blood cells from a PBC sample by adding saponin and/or ammonium chloride to a portion of the PBC sample, centrifuging the mixture, and washing the resulting pellet with water to remove residual blood proteins. However, these methods produce inconsistent identification of the microorganism at the species level across a panel of microorganisms and/or fail to identify *S. pneumoniae*. Furthermore, there is no indication that these methods result in a microbial pellet with sufficient viability to perform growth-based testing methods, such as AST.

Accordingly, it is desirable to develop reagents and methods that rapidly separate microorganism(s) from a PBC sample while maintaining the viability of the microorganism(s), so that analytical growth-based methods that require cell viability, such as AST testing, can be performed. Additionally, it is desirable that the reagents and methods can be used to isolate viable cells from all types of microorganism, including *S. pneumoniae*.

BRIEF SUMMARY OF THE INVENTION

Various embodiments of the disclosed invention provide for reagents and methods for rapidly isolating viable microbial cells from a PBC sample including *S. pneumoniae*. The resulting microbial pellet obtained using the various reagents and methods is sufficiently free from interfering substances and can be used for identification methods, such as MALDI-TOF/MS, growth-based identification and AST methods. This enables rapid results without the need for sub-culturing the microorganisms. The concentrated mass of viable microbial cells obtained by the various embodiments can be used for both the direct inoculation of rapid ID systems, such as MALDI-TOF/MS, and ID/AST testing (AST) by conventional or automated systems, such as the BD™ Phoenix™ ID/AST system. The various embodiments may also be applicable to other systems, molecular testing methods, such as polymerase chain reaction (PCR), and other methods known to one skilled in the art.

Described herein are various "lyse and wash" buffers that can be used for both lysing mammalian blood cells and washing away cellular debris and other blood components, while maintaining viability of the microorganism(s). The "lyse and wash" buffers described herein contain a base solution comprising, for example, salts, peptones, and other nutrients to protect the microorganism(s), as well as lytic reagents, such as detergents, thiols, and ammonium chloride to remove cellular debris from the mammalian blood cells.

The methods for isolating microorganism(s) from PBC samples described herein utilize the "lyse and wash" buffers to rapidly produce a pellet of viable microorganism that can be used for various downstream testing methods, for example, MALDI-TOF/MS identification and AST testing. The disclosed methods provide a process for rapidly isolating and concentrating microorganism(s) from PBC samples using one sample preparation tube, a single lyse step, a single wash step, and as little as one centrifugation step. These methods are easily adapted to automated systems and do not require sub-culturing of the microorganism in order to maintain cell viability.

The methods described herein do not utilize substances that interfere with methods for identifying the microorganism(s), for example mass spectrometry, or with phenotypic methods such as Phoenix™ ID. Furthermore, the methods described herein permit for the rapid isolation of viable microorganism(s) from a single PBC sample in sufficient quantity for use in multiple down-stream analysis, such as, identification by mass spectrometry, phenotypic or growth-based identification assays, and AST testing. Furthermore, the methods described herein prepare a sample for downstream analysis that will identify a wide panel of microorganisms, including the most difficult of organisms to characterize, for example, *S. pneumoniae*.

In another embodiment, a kit is provided which may include, for example, one or more of the "lyse and wash" buffers described herein for isolating viable microorganism(s) from a sample.

DETAILED DESCRIPTION

Figure 1:
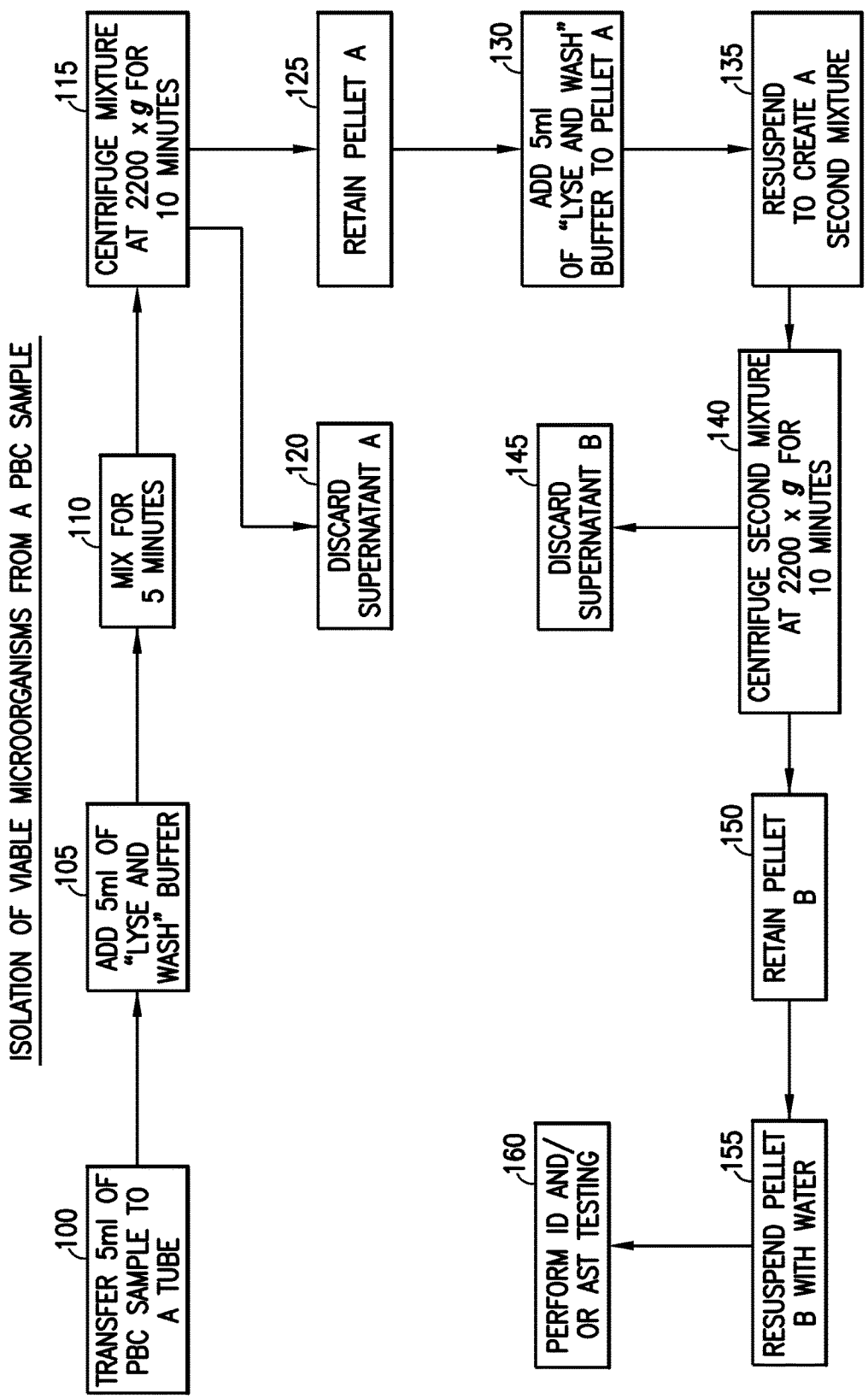
FIG. 1 demonstrates the method of one embodiment described herein for the isolation of viable microorganism(s) from a PBC sample.

Isolating and concentrating the microorganism(s) from PBC samples using the "lyse and wash" buffers and methods described herein maintains the viability of the microbial cells, and consequently their response to growth-based testing, such as AST testing. The methods described herein also reduce the amount of other substances in the sample, such as cellular debris, that may interfere with multiple identification methods such as MALDI-TOF/MS and Phoenix™ ID. In one embodiment, the buffers described herein are formulated to keep the concentration of salts at a minimum so as to prevent interference with MALDI-TOF/MS identification analysis.

In yet another embodiment, the buffers and methods described herein are used to isolate and perform downstream analysis on gram-positive bacteria, gram-negative bacteria, or yeast. In another embodiment, the gram-positive bacteria include *S. pneumoniae* as well as other species of Streptococci.

"Lyse and Wash" Buffer

The "lyse and wash" buffers described herein contain a balance of reagents that stabilize the microorganism(s) as well as lytic reagents for lysing blood cells. In one embodiment the buffer contains a base solution comprising salts, peptones, and other nutrients for stabilizing the microorganism(s) as well as non-ionic detergents, thiols, and optionally, ammonium chloride, for lysing blood cells in the sample.

Without being bound by a particular theory, it is believed that while the base solution may help to stabilize the microorganism(s), lytic reagents lyse the blood cells and remove interfering cellular debris. The "lyse and wash" buffers described herein provide for the potential for multiple independent lytic mechanisms: aqueous (osmotic lysis), detergents (membrane solubilization), thiols (disruption of protein-protein interactions in the membranes), and ammonium chloride (red blood cell membranes are effectively permeable to ammonium chloride and cell lysis occurs due to the unbalanced osmotic pressure of their colloid content). The combination of multiple lytic reagents allows for each of the lytic reagents to be less harsh on the microorganism(s) and can be used for a shorter duration than if used separately.

The base solution may contain a nutrient broth for microorganism(s), an isotonic buffer, peptones, and/or salts. The nutrient broth can be, for example, Trypticase™ soy broth. The formulation referred to as Trypticase™ soy broth used by applicants was: i) 17 grams (0.60 oz) of Tryptone; ii) 3 grams (0.11 oz) of Soy; iii) 5 grams (0.18 oz) of NaCl; iv) 2.5 grams (0.088 oz) of dipotassium phosphate ($K_2HPO_4$); and v) 2.5 grams (0.088 oz) of glucose. In one exemplary embodiment the concentration of the nutrient broth in the "lyse and wash" buffer is about 10 g/L to about 50 g/L. Isotonic buffers are clinical buffers known by one skilled in the art to be compatible with whole blood samples. Such buffers are typically mixtures of sodium phosphate, potassium phosphate, and saline, such as sodium chloride or phosphate buffered saline. In one exemplary embodiment, the concentration of isotonic buffer is about 1 g/L to about 85 g/L. In another exemplary embodiment, the isotonic buffer is a phosphate buffer. In one embodiment, the peptones include casein peptones and/or soy peptones. Additional constituents of the base solution contemplated include, for example, sodium pyruvate, yeast extract, sodium citrate, meat peptones, and/or dextrose.

In another embodiment, the "lyse and wash" buffer may contain a non-ionic detergent or mixtures of nonionic detergents. In this embodiment, at least one non-ionic detergent in the "lyse and wash" buffer is a non-ionic hemolytic detergent that selectively lyses blood cells but does not lyse the microorganism(s). Exemplary non-ionic hemolytic detergents contemplated include Triton™ X-100 (polyethylene glycol p-(1,1,3,3-tetramethylbutyl)-phenyl ether) and saponin. Other non-ionic detergents may include, for example, the Tween® family, the Brij® family, octyl-b-Glucoside, the Tergitol® family, the CYMAL® family, the MEGA family (including Noctanoyl-N-methylglucamine, N-nonanoyl, N-decanoyl), PLURONIC® family such as F-68, digitonins, and the CHAP family. In one exemplary embodiment, the concentration of non-ionic detergent(s) in the "lyse and wash" buffer is about 0.01 g/L to about 20 g/L. In another embodiment, the "lyse and wash" buffer contains Triton™ X-100 (polyethylene glycol p-(1,1,3,3-tetramethylbutyl)-phenyl ether) at a concentration of about 6.7 g/L.

In one embodiment, the "lyse and wash" buffer contains Triton™ X-100 (olyethylene glycol p-(1,1,3,3-tetramethylbutyl)-phenyl ether). The Triton™ X-100 (olyethylene glycol p-(1,1,3,3-tetramethylbutyl)-phenyl ether) concentration is selected to preserve the viability of S. pneumoniae. Exemplary embodiments contemplate concentrations of Triton™ X-100 (olyethylene glycol p-(1,1,3,3-tetramethylbutyl)-phenyl ether) of up to about 1 g/L. In another embodiment, the "lyse and wash" buffer contains Triton™ X-100 (polyethylene glycol p-(1,1,3,3-tetramethylbutyl)-phenyl ether) at a concentration of about 0.335 g/L. In still yet another embodiment, the "lyse and wash" buffer contains Triton™ X-100 (polyethylene glycol p-(1,1,3,3-tetramethylbutyl)-phenyl ether) at a concentration of about 0.1 g/L to about 1 g/l, about 0.1 g/L to about 0.9 g/l, about 0.1 g/L to about 0.8 g/l, about 0.1 g/L to about 0.7 g/l, about 0.1 g/L to about 0.6 g/l, about 0.1 g/L to about 0.5 g/l, about 0.1 g/L to about 0.4 g/l, about 0.2 g/L to about 1 g/l, about 0.3 g/L to about 1 g/l, about 0.2 g/L to about 0.9 g/l, about 0.2 g/L to about 0.8 g/l, about 0.2 g/L to about 0.7 g/l, about 0.2 g/L to about 0.6 g/l, about 0.2 g/L to about 0.5 g/l, about 0.2 g/L to about 0.4 g/l, about 0.3 g/L to about 0.9 g/l, about 0.3 g/L to about 0.8 g/l, about 0.3 g/L to about 0.7 g/l, about 0.3 g/L to about 0.6 g/l, about 0.3 g/L to about 0.5 g/l, or about 0.3 g/L to about 0.4 g/l. The "lyse and wash" buffers containing a concentration of Triton™ X-100 (polyethylene glycol p-(1,1,3,3-tetramethylbutyl)-phenyl ether) selected to preserve the viability of S. pneumoniae can also be used to isolate viable microbial cells from an organism other than S. pneumoniae without the need for a different "lyse and wash" buffer for these additional organisms.

In one embodiment, the "lyse and wash" buffer may optionally include ammonium chloride. In another embodiment, the concentration of ammonium chloride in the "lyse and wash" buffer is about 0.01 g/L to about 80 g/L.

Although the Applicant does not wish to be bound by a particular theory, the addition of ammonium chloride or other lytic components can help mitigate the effects of the other lytic components of the "lyse and wash" buffer on the viability of the microorganism. When using various lytic reagents, a sufficient quantity is needed in order to lyse the blood cells in the PBC sample. This often has the unwanted effect of causing microbial cell death. Detergents, thiols, and ammonium chloride employ different mechanisms of action for lysing blood cells. When combining multiple lytic mechanisms in one "lyse and wash" buffer, each of the different lytic components can potentially be used in a lower amount. This potentiality reduces the negative effect of lysing the microbial cells but may be sufficient for lysing the blood cells, resulting in more efficient blood cell lysis than when using each of the lytic ingredients alone. Therefore, microbial cell viability can be maintained while unwanted blood cell components can be eliminated.

In one embodiment the "lyse and wash" buffer contains a base solution comprising phosphate buffered saline, yeast extract, sodium citrate, meat peptones, dextrose, sodium pyruvate; thiols comprising sodium thioglycolate, and L-cysteine HCL; non-ionic detergents comprising saponin and Triton™ X-100 (polyethylene glycol p-(1,1,3,3-tetramethylbutyl)-phenyl ether); and optionally PBS.

In another embodiment the "lyse and wash" buffer contains a base solution comprising Trypticase™ soy broth (the formulation referred to as Trypticase™ soy broth used by applicants was: i) 17 grams (0.60 oz) of Tryptone; ii) 3 grams (0.11 oz) of Soy; iii) 5 grams (0.18 oz) of NaCl; iv) 2.5 grams (0.088 oz) of dipotassium phosphate ($K_2HPO_4$); and v) 2.5 grams (0.088 oz) of glucose), yeast extract, sodium citrate, meat peptones, sodium pyruvate; thiols comprising L-cysteine HCL and sodium thioglycolate; and non-ionic detergents comprising saponin and Triton™ X-100 (polyethylene glycol p-(1,1,3,3-tetramethylbutyl)-phenyl ether).

In yet another embodiment the "lyse and wash" buffer contains a base solution comprising Trypticase™ soy broth (the formulation referred to as Trypticase™ used by applicants was: i) 17 grams (0.60 oz) of Tryptone; ii) 3 grams (0.11 oz) of Soy; iii) 5 grams (0.18 oz) of NaCl; iv) 2.5 grams (0.088 oz) of dipotassium phosphate ($K_2HPO_4$); and v) 2.5 grams (0.088 oz) of glucose); thiols comprising L-cysteine HCL and sodium thioglycolate; and non-ionic detergents comprising saponin and Triton™ X-100 Polyethylene glycol p-(1,1,3,3-tetramethylbutyl)-phenyl ether.

In one embodiment the "lyse and wash" buffer comprises: a base solution comprising casein peptone at a concentration of about 8 g/L to about 35 g/L, sodium chloride at a concentration of about 2 g/L to about 10 g/L, soy peptone at a concentration of about 1.5 g/L to about 15 g/L, and potassium phosphate at a concentration of about 0.5 g/L to about 5 g/L; thiols comprising L-cysteine at a concentration of about 0.01 g/L to about 2.5 g/L and sodium thioglycolate at a concentration of about 0.01 g/L to about 2.5 g/L; and non-ionic detergents comprising saponin at a concentration of about 0.01 g/L to about 10 g/L and Triton™ X-100

(polyethylene glycol p-(1,1,3,3-tetramethylbutyl)-phenyl ether) at a concentration about 0.01 g/L to about 20 g/L.

In one embodiment the "lyse and wash" buffer comprises a base solution comprising casein peptone at a concentration of about 8 g/L to about 35 g/L, sodium chloride at a concentration of about 2 g/L to about 10 g/L, soy peptone at a concentration of about 1.5 g/L to about 15 g/L, and potassium phosphate at a concentration of about 0.5 g/L to about 5 g/L; thiols comprising L-cysteine at a concentration of about 0.01 g/L to about 2.5 g/L and sodium thioglycolate at a concentration of about 0.01 g/L to about 2.5 g/L; non-ionic detergents comprising saponin at a concentration of about 0.01 g/L to about 10 g/L and Triton™ X-100 (polyethylene glycol p-(1,1,3,3-tetramethylbutyl)-phenyl ether) at a concentration of about 0.01 g/L to about 20 g/L; and ammonium chloride at a concentration of about 0.01 g/L to about 80 g/L.

In one embodiment, an antifoaming agent can be optionally added to the "lyse and wash" buffer for manufacturing convenience. Preferably, the antifoaming agent has no demonstrable impact on performance of the "lyse and wash" buffer. Antifoaming agents are well known to those skilled in the art and are not described in detail herein. Selection of an antifoaming agent, and the amount, is largely a matter of design choice, and well within the capabilities of those skilled in the art based on the "lyse and wash" buffer requirements described herein. In one embodiment that antifoaming agent in the "lyse and wash" buffer is at a concentration of 0.1 g/L.

The concentrations of the various constituents of the "lyse and wash" buffers described herein represent the final concentrations of each constituent in the "lyse and wash" buffer. Often, a 1:1 volume ratio of PBC sample is mixed with the "lyse and wash" buffer; however, other volume ratios are contemplated. Accordingly, the concentrations of each constituent in the "lyse and wash" buffer can be adjusted to account for changes in the volume ratio of "lyse and wash" buffer to PBC sample in order to achieve a desired final concentration of the constituents of the "lyse and wash" buffer when mixed with the PBC sample.

In one embodiment, the "lyse and wash" buffer contains both saponin and Triton™ X-100 (polyethylene glycol p-(1,1,3,3-tetramethylbutyl)-phenyl ether) but does not contain an antifoaming agent. Without being bound by theory, the combination of saponin and Triton™ X-100 (polyethylene glycol p-(1,1,3,3-tetramethylbutyl)-phenyl ether) results in much less foaming of the treated PBC samples relative to using saponin as the sole non-ionic detergent in the "lyse and wash" buffer. This reduced foaming improves workflow, makes removal of the supernatant after centrifugation easier, and reduces or eliminates the need for antifoaming reagents (i.e., silicone fluids).

In one embodiment the "lyse and wash" buffer includes a choline-containing solution, for example, those choline-containing solutions as described in U.S. patent application Ser. No. 13/647,072, the contents of which are hereby incorporated herein by reference in their entirety. Although Applicant does not wish to be bound by a particular theory, the addition of a choline-containing solution to the "lyse and wash" buffer may inhibit, prevent, and/or mitigate autolysis of the microorganism, particularly S. pneumonia, in the presence of lytic components of the "lyse and wash" buffer.

In another embodiment, a kit is provided which may comprise, for example, one or more of the "lyse and wash" buffers described herein for isolating viable microorganism(s) from a PBC sample.

Methods for Isolating Microorganism(s) from a PBC Sample

The methods for isolating microorganism(a) from a sample suspected of containing at least one microorganism, for example a PBC sample, described herein may utilize the various "lyse and wash" buffers contemplated to rapidly produce a viable microbial pellet that can be used for various downstream testing methods, such as, identification by MALDI-TOF/MS, growth-based phenotypic assays and AST testing. In one embodiment, the method includes adding a portion of a PBC sample with the "lyse and wash" buffer to form a mixture. In one embodiment the volume ratio of PBC sample to "lyse and wash" buffer is 1:1. The mixture is incubated for a period of time to lyse the blood cells in the BPC sample.

In one embodiment the "lyse and wash" buffer mixed with the portion of the PBC sample comprises at least one non-ionic detergent at a concentration of about 0.01 g/L to about 20 g/L. In another embodiment, the "lyse and wash" buffer contains Triton™ X-100 (polyethylene glycol p-(1,1,3,3-tetramethylbutyl)-phenyl ether) at a concentration of about 6.7 g/L. In yet another embodiment, the "lyse and wash" buffer contains Triton™ X-100 (polyethylene glycol p-(1,1,3,3-tetramethylbutyl)-phenyl ether) at a concentration up to about 1 g/L. In yet another embodiment, the "lyse and wash" buffer contains Triton™ X-100 (Polyethylene glycol p-(1,1,3,3-tetramethylbutyl)-phenyl ether) at about 0.335 g/L. In still yet another embodiment, the "lyse and wash" buffer contains Triton™ X-100 (polyethylene glycol p-(1,1,3,3-tetramethylbutyl)-phenyl ether) at a concentration of range of about 0.1 g/L to about 1 g/l, about 0.1 g/L to about 0.9 g/l, about 0.1 g/L to about 0.8 g/l, about 0.1 g/L to about 0.7 g/l, about 0.1 g/L to about 0.6 g/l, about 0.1 g/L to about 0.5 g/l, about 0.1 g/L to about 0.4 g/l, about 0.2 g/L to about 1 g/l, about 0.3 g/L to about 1 g/l, about 0.2 g/L to about 0.9 g/l, about 0.2 g/L to about 0.8 g/l, about 0.2 g/L to about 0.7 g/l, about 0.2 g/L to about 0.6 g/l, about 0.2 g/L to about 0.5 g/l, about 0.2 g/L to about 0.4 g/l, about 0.3 g/L to about 0.9 g/l, about 0.3 g/L to about 0.8 g/l, about 0.3 g/L to about 0.7 g/l, about 0.3 g/L to about 0.6 g/l, about 0.3 g/L to about 0.5 g/l, or about 0.3 g/L to about 0.4 g/l.

In one embodiment, after the mixture is prepared from combining a portion of the PBC sample with "lyse and wash" buffer, the mixture is incubated for up to about 5 minutes. In another embodiment the mixture is inverted several times during incubation to ensure even mixing of the PBC sample and "lyse and was" buffer. After incubation, the mixture is centrifuged to form a pellet containing viable microorganism(s) and a supernatant containing blood cell debris. The range of speed and time of centrifugation may be optimized in order to achieve a readily discernible pellet in order to easily remove the supernatant without disturbing the pellet. Various variables will affect the speed and time of centrifugation including, for example, volume of the mixture, size and shape of the sample tube, and type of rotor. In one embodiment the mixture is centrifuged at a speed of about 100×g to about 5000×g. In another embodiment the mixture is centrifuged for up to and including about 10 minutes.

After centrifugation the supernatant is discarded while the pellet is washed with a second volume of the "lyse and wash" buffer. The "lyse and wash" buffer used for the washing step can be the same or different formulation than the "lyse and wash" buffer used for lysing the blood cells in the lysing step. After washing the pellet, the mixture is centrifuged for a second time. The supernatant, containing blood cell debris, is again discarded while the pellet, containing viable microorganism is retained. Trace liquids from the top of the pellet can be removed. Lastly, the pellet may be resuspended in a solution for downstream analysis. In one embodiment, the pellet is resuspended in a solution at a concentration of at least about 4 McFarland.

The viable microbial pellet resulting from the various embodiments described herein can be used to prepare a common sample for various downstream testing methods including identification by mass spectrometry, for example, MALDI-TOF/MS identification, phenotypic growth-based identification, for example, Phoenix™ ID, and AST testing, for example, Phoenix™ AST testing. In addition, the entire method can be performed in one sample tube without the need for transferring sample between multiple tubes. Therefore, the methods described herein are readily adaptable to automated systems.

Techniques such as higher PBC sample volume, multiple aliquots of PBC sample, multiple spins, etc., described herein can be deployed to increase the number of microorganism(s) in the starting volume to improve yield. In addition, these methods provide a rapid sample preparation method and are easily automated. Furthermore, the methods and buffers described herein subject the blood cells to lysis, remove interfering substances from the PBC sample, and provide high yields of viable microorganism(s). In one embodiment, the yield of viable microbial pellet can be increased by increasing the starting volume of PBC sample and/or by performing the isolation method on several aliquots from one PBC sample and combining the resulting microbial pellets into one sample.

FIG. 1 illustrates one embodiment of the methods described herein. A portion of a PBC sample, for example 5 ml, is transferred (100) to a sample tube. A volume of "lyse and wash" buffer, for example 5 ml, is added (105) to the PBC sample and mixed (110), for example for 5 minutes. The mixture is centrifuged (115), for example at 2200×g for 10 minutes, resulting in pellet A containing viable microorganism(s) and supernatant A containing blood cell debris. Supernatant A is decanted and discarded (120) while pellet A is retained (125). A second volume of "lyse and wash" buffer, for example 5 ml, is added (130) to pellet A to resuspend the pellet. Resuspended pellet A is mixed (135) to create a second mixture. The second mixture is centrifuged (140), for example at 2200×g for 10 minutes, resulting in pellet B containing viable microorganism(s) and supernatant B containing additional blood cell debris not removed by the first centrifugation step (115). Supernatant B is decanted and discarded (145) while pellet B is retained (150). At least a portion of pellet B is resuspended (155) in a liquid, for example, with 600 µl of sterile deionized water, to achieve a dense microbial suspension, for example a suspension of approximately 4 McFarland. The resulting microbial suspension can be used for various downstream testing methods (160) such as, for example, identification by MALDI/TOF-MS and phenotypic growth-based identification, for example, identification by the Phoenix™ system, and growth-based AST methods such as Phoenix™ AST testing.

In one embodiment of the methods for isolating viable microorganism described herein, the PBC sample is incubated with a choline solution prior to or simultaneously with the "lyse and wash" buffers as described in U.S. patent application Ser. No. 13/647,072, the contents of which is incorporated herein by reference in its entirety.

In another embodiment, methods are provided for the isolation of viable S. pneumoniae from a PBC sample. These methods include obtaining a blood sample suspected of containing at least one microorganism. A portion of the blood sample is added to an anaerobic blood culture bottle while a second portion of the blood sample is added to an aerobic blood culture bottle. The bottles are incubated until a positive signal is obtained. An early indication of the presence of S. pneumoniae in the blood sample is obtained by combining a portion of a aerobic PBC sample with the "lyse and wash" buffer described herein to form a mixture, incubating the mixture for a period of time to lyse the blood cells, and centrifuging the mixture to form a pellet. A pellet that is green in color provides an early indication of the presence of S. pneumoniae in the blood sample. In the alternative an early indication of the presence of S. pneumoniae in the blood sample is obtained by visually observing the aerobic positive blood culture bottle for a solution green in color.

After this early indication of S. pneumoniae, the anaerobic PBC sample may be used to isolate viable S. pneumoniae for downstream analysis using any of the methods described herein for the isolation of viable microorganism. In one embodiment, the method includes adding a portion of an anaerobic PBC sample with the "lyse and wash" buffer described herein to form a mixture. The mixture is incubated for a period of time to lyse the blood cells in the BPC sample.

In one embodiment, the methods for isolating viable S. pneumoniae include the use of a "lyse and wash" buffer containing Triton™ X-100 (polyethylene glycol p-(1,1,3,3-tetramethylbutyl)-phenyl ether). The Triton™ X-100 (polyethylene glycol p-(1,1,3,3-tetramethylbutyl)-phenyl ether) concentration is selected to preserve the viability of the S. pneumoniae. A concentration of up to about 1 g/L is contemplated. In another embodiment, the methods for isolating viable S. pneumoniae include the use of a "lyse and wash" buffer containing Triton™ X-100 (polyethylene glycol p-(1,1,3,3-tetramethylbutyl)-phenyl ether) of about 0.335 g/L.

In one embodiment, after the mixture is prepared from combining a portion of the PBC sample with "lyse and wash" buffer, the mixture is incubated for up to and including about 5 minutes. In another embodiment the mixture is inverted several times during incubation to ensure even mixing of the PBC sample and "lyse and was" buffer. After incubation, the mixture is centrifuged to form a pellet containing viable microorganism(s) and a supernatant containing blood cell debris.

After centrifugation the supernatant is discarded while the pellet, containing viable S. pneumoniae, is washed with a second volume of the "lyse and wash" buffer. The "lyse and wash" buffer used for the washing step can be the same or different formulation than the "lyse and wash" buffer used for lysing the blood cells in the lysing step. After washing the pellet, the mixture is centrifuged for a second time. The supernatant, containing blood cell debris, is again discarded while the pellet, containing viable S. pneumoniae, is retained. Lastly, the pellet may be resuspended in a solution for downstream analysis.

Figure 2:
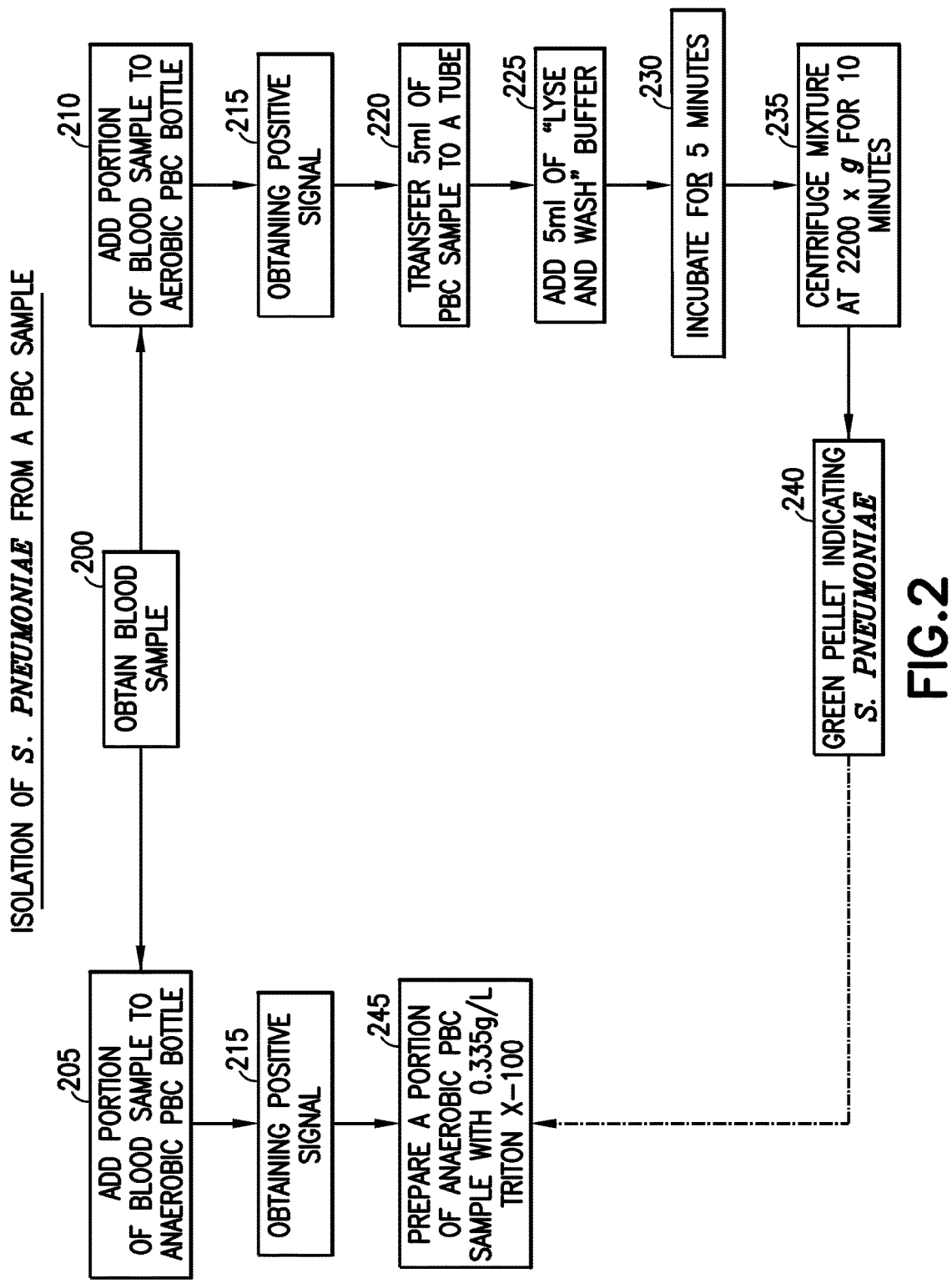
FIG. 2 demonstrates the method of one embodiment described herein for the isolation of viable *S. pneumoniae* from a PBC sample.

One embodiment of the method for isolating viable S. pneumoniae from a PBC sample is illustrated in FIG. 2. A blood sample that is suspected of containing S. pneumoniae is obtained (200). A portion of the blood sample (for example 10 ml) is added (205) to an anaerobic blood culture bottle while a second portion of the blood sample (for example 10 ml) is added (210) to an aerobic blood culture bottle. A positive signal is obtained (215) in both the anaerobic and aerobic PBC bottles indicating the presence of a microorganism. A portion of the aerobic PBC sample, for example 5 ml, is transferred (220) to a tube. A volume of the "lyse and wash" buffer described herein containing a concentration of Triton™ X-100 (polyethylene glycol p-(1,1,3,3-tetramethylbutyl)-phenyl ether) selected to preserve the viability of *S. pneumoniae*, for example 0.335 g/L Triton™ X-100 (polyethylene glycol p-(1,1,3,3-tetramethylbutyl)-phenyl ether), for example 5 ml, is added (225) to the PBC sample to form a mixture. The mixture is incubated (230) for a period of time (for example 5 minutes) to lyse the blood cells. The mixture is then centrifuged (235) to form a pellet green in color which provides an early indication (240) of the presence of *S. pneumoniae* in the blood sample. After an early indication of *S. pneumoniae* (240) a portion of the anaerobic PBC sample is prepared (245) for downstream analysis using any of the methods described herein for isolating viable microorganism from a PBC sample, including, for example, the methods described in FIG. 1 using a "lyse and wash" buffer containing a concentration of Triton™ X-100 (polyethylene glycol p-(1,1,3,3-tetramethylbutyl)-phenyl ether) selected to preserve the viability of *S. pneumoniae*, for example 0.335 g/L of Triton™ X-100 (polyethylene glycol p-(1,1,3,3-tetramethylbutyl)-phenyl ether).

EXAMPLES

Example 1

Positive blood culture samples were obtained by inoculating a blood culture bottle with *Enterobacter aerogenes* (ATCC 13048) or *Staphylococcus aureus* (ATCC 43300 MRSA) and incubating until a positive signal was indicated. A portion to the PBC sample (5 ml) was directly withdrawn from the bottle and placed into a 15 ml conical tube. Choline chloride (0.5 ml of 20% choline chloride solution) was added to the PBC sample, incubated at room temperature for 20 minutes, and centrifuged at 132×g for 5 minutes in a Beckman J6-MI centrifuge with a JS-4.2 rotor. The supernatant was transferred to a second 15 ml conical tube and mixed with 5 ml of a "lyse and wash" buffer containing 16 g/L ammonium chloride 6.7 g/L Triton™ X-100 (polyethylene glycol p-(1,1,3,3-tetramethylbutyl)-phenyl ether), and BD Bactec Lytic 10 (catalog number 442265). The mixture was incubated for 5 minutes at room temperature. The lysed sample was then centrifuged at 1855×g for 10 minutes. After removing the supernatant, the remaining bacteria pellet was resuspended in 4.5 ml BD Phoenix™ ID broth (Catalog number 246001). A portion of the recovered microorganism was used to determine viability of the organism by plate count. The results of the viability testing by plate count indicated $1.85 \times 10^9$ cfu/ml of *E. aerogenes* after lysis compared to $1.65 \times 10^9$ cfu/ml for the PBC sample prior to lysis. Viability testing also demonstrated $1.25 \times 10^8$ cfu/ml for *S. aureus* after lysis compared to $2.00 \times 10^8$ cfu/ml for the PBC sample prior to lysis.

A second portion of the recovered bacterial suspension was then further diluted with the BD Phoenix™ ID broth to a concentration of 0.5 McFarland and used for Phoenix™ ID/AST testing. The BD Phoenix™ ID/AST System is described in, e.g., U.S. Pat. Nos. 5,922,593, 6,096,272, 6,372,485, 6,849,422, and 7,115,384, the contents of which are hereby incorporated herein by reference. A portion of the inoculum prepared above was used for phenotypic identification by Phoenix™ ID and was poured into the identification portion of a BD Phoenix™ ID/AST panel (Becton, Dickinson and Company) and sealed with a plastic closure. A second portion of the inoculum prepared above was used for AST testing by Phoenix™ AST and was poured into the AST portion of a BD Phoenix™ ID/AST panel (Becton, Dickinson and Company) and sealed with a plastic closure. The antimicrobial susceptibility minimal inhibitory concentration (MIC) for a series of antibiotics was calculated for each of the isolated microbial pellets. The MIC results from the microbial pellets were compared to the MIC results from the same strains obtained from plated pure cultures ("Control"). This comparison indicates whether the Test Method provides substantially equivalent results to the Control Method, i.e., the rate of essential agreement (EA) between the Test Method and the Control Method. A dilution difference of 0 indicates exact agreement between the Test Method and the Control Method. A dilution difference of −1 or +1 indicates that the Test Method is considered within EA to the Control Method, i.e., within normal test variation. Dilution differences outside this range, such as for example −4, +4, −3, +3, −2 and +2, indicates the results are not within essential agreement for the antibiotic/microorganism tested. The methods and verification of AST results are further described in "Verification and Validation of Procedures in the Clinical Microbiology Laboratory", Cumitech 31, (February 1997, ASM Press).

Recovered bacteria from both PBC samples resulted in a correct Phoenix™ identification as *E. aerogenes* and *S. aureus* with both samples having a 99% confidence value. The Phoenix™ AST results showed 100% essential agreement (EA) when compared with those samples prepared from plated colonies, i.e., the dilution difference was within −1 to +1 dilution difference. The *S. aureus* AST results included correct identification of the four (4) resistance markers expected for this MRSA strain, including methicillin resistant *staphylococcus* (MRS), mecA-mediated resistant *staphylococcus* (mecA), beta-lactamase-producing *staphylococcus* (BLACT), and *staphylococcus* MLSb phenotype (STAMLS).

These results demonstrate that the "lyse and wash" buffers described herein can be used to isolate viable microorganism from a PBC sample for downstream identification and AST testing.

Example 2

Four positive blood culture samples were obtained by inoculating a blood culture bottle with either *Enterococcus faecium* (ATTC 700221), *Enterococcus faecalis* (ATCC 51299), *Staphylococcus aureus* (ATCC 43300), or *Proteus mirabilis* (ATCC 29906). Four different "lyse and wash" buffers were prepared comprising the formulations summarized in Table 1 below.

TABLE 1

| Buffer #1 | Bactec Lytic 10 media and 6.7 g/L Triton ™ X-100 (polyethylene glycol p-(1,1,3,3-tetramethylbutyl)-phenyl ether) |
|---|---|
| Buffer #2 | Bactec Lytic 10 media, 3.35 g/L Triton ™ X-100, and (polyethylene glycol p-(1,1,3,3-tetramethylbutyl)-phenyl ether), and 16 g/L ammonium chloride |
| Buffer #3 | Bactec Lytic 10 media, 3.35 g/L Triton ™ X-100, and (polyethylene glycol p-(1,1,3,3-tetramethylbutyl)-phenyl ether), and 40 g/L ammonium chloride |

TABLE 1-continued

| | |
|---|---|
| Buffer #4 | Bactec Lytic 10 media, 3.35 g/L Triton ™ X-100, and (polyethylene glycol p-(1,1,3,3-tetramethylbutyl)-phenyl ether), and 80 g/L ammonium chloride |

Each of the four "lyse and wash" buffers were used to prepare a microbial pellet from each of the four PBC samples for a total of 16 samples prepared. To isolate viable microorganism, a portion of each PBC sample (5 ml) was pre-treated with 0.5 ml of a 20% choline chloride solution for 20 minutes in a 15 ml conical tube. After incubation with the choline chloride solution, 8 ml of each "lyse and wash" buffer was added to the sample and mixed for 10 minutes. The sample was then centrifuged at 1855×g for 10 minutes. The supernatant was decanted and discarded while the pellet was washed by resuspending the pellet in the same tube with 5 ml 3.4 g/L Triton™ X-100 (polyethylene glycol p-(1,1,3,3-tetramethylbutyl)-phenyl ether) in BD Bactec Lytic 10 media (catalog number 442265) without ammonium chloride. The resuspended pellet was allowed to mix for 5 minutes followed by centrifugation at 3000 rpm 1855×g for 10 minutes. The supernatant was removed and discarded while the pellet was used for both MADLI-TOF/MS identification and Phoenix™ ID/AST testing as described below.

A portion of the bacterial pellet prepared above was resuspended in a microcentrifuge tube containing 0.6 ml sterile deionized water. A portion of the suspension (1 μl) was spotted onto a MALDI-TOF/MS target plate for bacterial identification analysis and allowed to air dry. Formic acid (1-2 μl of a 70% aqueous solution) was overlaid onto the dried, spotted sample and allowed to air dry. The dried sample was overlaid with 1 μl of MALDI-TOF/MS matrix solution (MALDI-MS matrix solution prepared by dissolving 2.5 mg of HCCA in 250 μl of 2.5% trifluoroacetic acid and 47.5% acetonitrile in de-ionized water) and allowed to air dry before identification by MALDI-TOF mass spectrometry. All mass spectrometry data was recorded on a Bruker Microflex™ LT with Biotyper 2.0 software. The methods of preparing the isolated microbial pellet and identifying the microorganism by the mass spectrometry are further described in U.S. application Ser. No. 13/636,944, filed Aug. 31, 2012, which is hereby incorporated herein by reference. A MALDI-TOF/MS score greater than or equal to 2.0 indicates identification to the species level. A MALDI-TOF/MS score between 1.7 and 1.999 indicates identification to the genus level. And a MALDI-TOF/MS score less than 1.7 indicates no identification or a non-reliable identification. The results are summarized in Table 2 below. A "yes" indicates that a correct identification was obtained at least to the genus level, i.e., with a MALDI score of at least 1.7.

A second portion of the suspension prepared for MALDI-TOF/MS as described above was further diluted with Phoenix™ ID broth to approximately 0.5 McFarland and used to inoculate a Phoenix™ AST panel as described in Example 1. The results are summarized in Table 2 below. For the Phoenix™ AST results, a "yes" represents those samples that were in essential agreement between the control sample (plated colonies), i.e., those samples with a dilution difference of only +1 or −1.

TABLE 2

| | MALDI-TOF/MS Identification | Phoenix ™ AST |
|---|---|---|
| Buffer #1 E. faecium | Yes | Yes |
| Buffer #1 E. faecalis | Yes | Yes |
| Buffer #1 S. aureus | Yes | Yes |
| Buffer #1 P. mirabilis | Yes | Yes |
| Buffer #2 E. faecium | Yes | Yes |
| Buffer #2 E. faecalis | Yes | Yes |
| Buffer #2 S. aureus | Yes | Yes |
| Buffer #2 P. mirabilis | Yes | Yes |
| Buffer #3 E. faecium | Yes | Yes |
| Buffer #3 E. faecalis | Yes | Yes |
| Buffer #3 S. aureus | Yes | Yes |
| Buffer #3 P. mirabilis | Yes | Yes |
| Buffer #4 E. faecium | Yes | Yes |
| Buffer #4 E. faecalis | Yes | Yes |
| Buffer #4 S. aureus | Yes | Yes |
| Buffer #4 P. mirabilis | No | Yes |
| Total | 15/16 | 16/16 |

The results demonstrate that various "lyse and wash" buffers can be used to isolate viable microorganism from a PBC sample for downstream identification by mass spectrometry and AST testing across a panel of microorganisms.

Example 3

Three positive blood culture samples were obtained by inoculating a blood culture bottle with either *Enterococcus faecalis* (VRE ATCC 51299), *Klebsiella pneumoniae* (ATCC 700603), or *Staphylococcus aureus* (ATCC 43300). Two different "lyse and wash" buffers were prepared comprising the formulations summarized in Table 3 below. The only difference between buffer #1 and buffer #2 was the addition of 16 g/L ammonium chloride in buffer #2.

TABLE 3

| | |
|---|---|
| Buffer #1 | 27.5 g/L Trypticase ™ Soy Broth (the formulation referred to as Trypticase ™ used by applicants was: i) 17 grams (0.60 oz) of Tryptone; ii) 3 grams (0.11 oz) of Soy; iii) 5 grams (0.18 oz) of NaCl; iv) 2.5 grams (0.088 oz) of dipotassium phosphate (K2HPO4); and v) 2.5 grams (0.88 oz) of glucose), 0.7 g/L L-Cysteine HCl, 0.3 g/L Sodium Thioglycolate, 2.6 g/L Saponin, and 6.7 g/L Triton ™ X-100. 100 (polyethylene glycol p-(1,1,3,3-tetramethylbutyl)-phenyl ether). |
| Buffer #2 | 27.5 g/L Trypticase ™ Soy Broth, (the formulation referred to as Trypticase ™ used by applicants |

TABLE 3-continued

| | |
|---|---|
| | was: i) 17 grams (0.60 oz) of Tryptone; ii) 3 grams (0.11 oz) of Soy; iii) 5 grams (0.18 oz) of NaCl; iv) 2.5 grams (0.088 oz) of dipotassium phosphate (K2HPO4); and v) 2.5 grams (0.88 oz) of glucose), 0.7 g/L L-Cysteine HCl, 0.3 g/L Sodium Thioglycolate, 2.6 g/L Saponin, 6.7 g/L Triton ™ X-100, and 100 (polyethylene glycol p-(1,1,3,3-tetramethylbutyl)-phenyl ether), and 16 g/L ammonium chloride. |

Each of the "lyse and wash" buffers of Table 3 were used to prepare a microbial pellet from each of the three PBC samples for a total of six samples prepared. A portion of each PBC sample (5 ml) was mixed with 5 ml of each "lyse and wash" buffer. The samples were then centrifuged at 2200×g for 10 minutes. The supernatant was decanted and discarded while the pellet was washed by resuspending the pellet in the same tube with the same "lyse and wash" buffer. The resuspended pellet was centrifuged at 2200×g for 10 minutes. The supernatant was removed and discarded while the pellet was used for both MADLI-TOF/MS identification and Phoenix™ ID/AST testing as described below.

A portion of the bacterial pellet was resuspended in a microcentrifuge tube containing 0.6 ml sterile water. A portion of the suspension (1 µl) was spotted onto a MALDI-TOF/MS target plate for bacteria identification analysis as described in Example 2. The results are summarized in Table 4 below and indicate whether a correct identification was obtained at least to the genus level, i.e., with a MALDI score of at least 1.7. A second portion of the suspension prepared for MALDI-TOF/MS above was further diluted with Phoenix™ ID broth to approximately 0.5 McFarland and used to inoculate a Phoenix™ ID panel as described in Example 1. The results are summarized in Table 4 below.

TABLE 4

| | MALDI-TOF/MS Identification | Phoenix ™ Identification |
|---|---|---|
| Buffer #1 E. faecalis | Yes | Yes |
| Buffer #1 K. pneumoniae | Yes | Yes |
| Buffer #1 S. aureus | Yes | Yes |
| Buffer #2 E. faecalis | Yes | Yes |
| Buffer #2 K. pneumoniae | Yes | Yes |
| Buffer #2 S. aureus | Yes | Yes |
| Total | 6/6 | 6/6 |

The results demonstrate that various "lyse and wash" buffers, with or without ammonium chloride, can be used to isolate viable microorganism from a PBC sample for downstream identification across a panel of microorganisms.

Example 4

Tests were performed to determine the viability of several different strains of S. pneumoniae upon exposure to various "lyse and wash" buffers described herein. Additional tests were performed to determine whether processing a PBC sample with these various "lyse and wash" buffers sufficiently removes substances that interfere with identification of the microorganism.

Cell Viability

Three different "lyse and wash" buffers were prepared as summarized in Table 5 below, each with a different amount of Triton™ X-100 (polyethylene glycol p-(1,1,3,3-tetramethylbutyl)-phenyl ether), i.e., 6.7 g/L, 0 g/L, or 0.335 g/L.

TABLE 5

| | |
|---|---|
| Buffer #1 (high Triton ™ X-100) (polyethylene glycol p-(1,1,3,3-tetramethylbutyl)-phenyl ether) | 27.5 g/L Trypticase ™ soy broth (the formulation referred to as Trypticase ™ soy broth used by applicants was: i) 17 grams (0.60 oz) of Tryptone; ii) 3 grams (0.11 oz) of Soy; iii) 5 grams (0.18 oz) of NaCl; iv) 2.5 grams (0.88 oz) of dipotassium phosphate (K2HPO4); and v) 2.5 grams (0.88 oz) of glucose), 0.7 g/L L-cysteine HCL, 0.3 g/L sodium thioglycolate, 2.6 g/l saponin, 6.7 g/L Triton ™ X-100. 100 (polyethylene glycol p-(1,1,3,3-tetramethylbutyl)-phenyl ether). |
| Buffer #2 (no Triton ™ X-100) (polyethylene glycol p-(1,1,3,3-tetramethylbutyl)-phenyl ether) | 27.5 g/L Trypticase ™ soy broth with glucose (the formulation referred to as Trypticase ™ soy broth used by applicants was: i) 17 grams (0.60 oz)of Tryptone; ii) 3 grams (0.11 oz) of Soy; iii) 5 grams (0.18 oz) of NaCl; iv) 2.5 grams (0.88 oz) of dipotassium phosphate (K2HPO4); and v) 2.5 grams (0.88 oz) of glucose), 0.7 g/L L-cysteine HCL, 0.3 g/L sodium thioglycolate, 2.6 g/l saponin |
| Buffer #3 (low Triton ™ X-100) (polyethylene glycol p-(1,1,3,3-tetramethylbutyl)-phenyl ether) | 27.5 g/L Trypticase ™ soy broth with glucose, (the formulation referred to as Trypticase ™ soy broth used by applicants was: i) 17 grams (0.60 oz)of Tryptone; ii) 3 grams (0.11 oz) of Soy; iii) 5 grams (0.18 oz) of NaCl; iv) 2.5 grams (0.88 oz) of dipotassium phosphate (K2HPO4); and v) 2.5 grams (0.88 oz) of glucose), 0.7 g/L L-cysteine HCL, 0.3 g/L sodium thioglycolate, 2.6 g/l saponin, and 0.335 g/L Triton ™ X-100. (polyethylene glycol p-(1,1,3,3-tetramethylbutyl)-phenyl ether). |

A volume of each of these buffers (10 ml) was inoculated with $1 \times 10^3$ cfu/ml of either S. pneumoniae non-mucoidal strain (POS3092) or S. pneumoniae mucoidal strain (POS650) and incubated for up to four hours. As a positive control, a 10 ml volume of anaerobic nutrient broth was also inoculated with each of the S. pneumoniae strains, as the microorganisms would be expected to grow in this nutrient broth. After inoculation at the time points of 0 hour, 1 hour, 2 hour, and 4 hour, a 100 µl volume of the mixture was plated onto agar plates containing 5% sheep blood at a density of approximately $1 \times 10^2$ cfu/plate. The plates were incubated overnight at 35° C./5% $CO_2$ at which time the plates were manually counted for bacterial colonies. The results of the manual plate count are summarized in Table 6 below.

TABLE 6

|  | Buffer | 0 hour | 1 hour | 2 hour | 4 hour |
|---|---|---|---|---|---|
| S. pneumoniae Non-mucoidal (POS3092) | #1 (high) | 23 | 0 | 0 | 0 |
|  | #2 (no) | 82 | 105 | 125 | 101 |
|  | #3 (low) | 105 | 100 | 70 | 31 |
|  | Anaerobic Broth (Control) | 149 | 130 | 98 | 113 |
| S. pneumoniae mucoidal (POS650) | #1 (high) | 10 | 0 | 0 | 0 |
|  | #2 (no) | 28 | 37 | 19 | 17 |
|  | #3 (low) | 36 | 38 | 33 | 28 |
|  | Anaerobic Broth (Control) | 70 | 67 | 74 | 57 | a Nutator™ for 5 minutes. The mixture was centrifuged at 2200×g for 10 minutes followed by decanting and discarding of the supernatant. To wash the pellet of residual blood cell debris, an additional 5 ml of the same "lyse and wash" buffer was added to the tube and vortexed to resuspend the pellet. The mixture was centrifuged at 2200×g for 10 minutes. The supernatant was decanted and excess liquid removed from the resulting microbial pellet using a cotton applicator swab. The microbial pellet was resuspended in 600 µl sterile deionized water to achieve an inoculum of microbial suspension of approximately 4 McFarland.

The resulting pellet was prepared for identification by MALDI-TOF/MS by the methods described in Example 2 above. The MADLI-TOF/MS scores are summarized in Table 7 below.

TABLE 7

| Buffer | S. pneumoniae Non-mucoidal (POS3092) | S. pneumoniae Non-mucoidal (POS3996) | S. pneumoniae Non-mucoidal (POS3999) | S. pneumoniae mucoidal (POS650) | S. pneumoniae mucoidal (POS532) |
|---|---|---|---|---|---|
| Aerobic Bottle/ Buffer #1 (high) | 1.65 1.71 1.633 | 1.859 1.647 1.814 | 1.558 1.442 1.587 | 1.427 1.516 1.281 | 1.57 1.371 1.372 |
| Anaerobic Bottle/ Buffer #2 (no) | 1.982 0 1.479 | 2.179 2.251 2.185 | 2.248 2.143 2.02 | 1.698 0 1.799 | 1.682 1.782 1.779 |
| Aerobic Bottle/ Buffer #2 (no) | 1.899 1.594 1.729 | 1.204 1.338 1.524 | 1.817 1.837 1.769 | 1.44 1.377 1.269 | 1.408 1.345 1.313 |
| Anaerobic Bottle/ Buffer #3 (low) | 1.983 1.891 1.856 | 2.286 2.309 2.202 | 2.453 2.441 2.458 | 2.213 2.066 2.1 | 1.972 2.085 2.205 |
| Aerobic Bottle/ Buffer #3 (low) | 1.952 2.002 2.092 | 2.276 1.971 2.101 | 2.114 2.253 2.18 | 1.428 1.415 1.329 | 1.206 1.375 1.389 |

As Table 6 demonstrates, viable S. pneumoniae were not obtained following a 1 hour exposure to a high concentration of Triton™ X-100 (polyethylene glycol p-(1,1,3,3-tetramethylbutyl)-phenyl ether) (buffer #1). However, comparable amounts of viable S. pneumoniae were obtained using the no Triton™ X-100 (polyethylene glycol p-(1,1,3,3-tetramethylbutyl)-phenyl ether) (#2) and low Triton™ X-100 (polyethylene glycol p-(1,1,3,3-tetramethylbutyl)-phenyl ether) (#3) buffers.

Identification by MALDI-TOF/MS

The various "lyse and wash" buffers of Table 5 were used to prepare a bacterial pellet from a PBC sample to be used for identification by MALDI-TOF/MS to determine whether the various "lyse and wash" buffers sufficiently cleaned the PBC sample from interfering cellular debris. PBC samples were prepared with five different strains of S. pneumoniae including non-mucoidal strain POS3092, non-mucoidal strain POS3996, non-mucoidal strain POS3999, mucoidal strain POS650, and mucoidal strain POS532 by inoculating both an aerobic and anaerobic bottle for each of the strains. The microorganism was isolated from each of the PBC samples using each of the "lyse and wash" buffers of Table 5 by adding to each PBC sample a volume of the lyse and wash" buffer at a ratio of 1:1. The mixtures were mixed on The results indicate that preparation of a viable microbial pellet from an anaerobic PBC bottle produced significantly better MALDI scores for various strains of S. pneumoniae compared to the pellets prepared from the aerobic PBC bottle. In addition, the "lyse and wash" buffers described herein containing low amounts of Triton™ X-100 (polyethylene glycol p-(1,1,3,3-tetramethylbutyl)-phenyl ether) produce significantly better MALDI scores across the entire panel of S. pneumoniae strains compared to samples prepared with a high concentration of Triton™ X-100 (polyethylene glycol p-(1,1,3,3-tetramethylbutyl)-phenyl ether).

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A buffer for isolating and concentrating viable microorganisms from a positive blood culture sample consisting of:
    a nutrient base solution;
    at least one non-ionic detergent;

optionally, ammonium chloride; and at least one thiol, wherein the relative amounts of the nutrient base solution, the at least one non-ionic detergent, and the at least one thiol in the buffer are selected to preserve the viability of *S. pneumoniae,* wherein the nutrient base solution consists of casein peptone at a concentration in the buffer of about 8 g/L to about 35 g/L, sodium chloride at a concentration in the buffer of about 2 g/L to about 10 g/L, soy peptone at a concentration in the buffer of about 1.5 g/L to about 15 g/L, and potassium phosphate at a concentration in the buffer of about 0.5 g/L to about 5 g/L and optionally at least one other nutrient;

the at least one thiol consisting of L-cysteine at a concentration in the buffer of about 0.01 g/L to about 2.5 g/L and sodium thioglycolate at a concentration in the buffer of about 0.01 g/L to about 2.5 g/L; and the at least one non-ionic detergent consisting of saponin at a concentration in the buffer of about 0.01 g/L to about 10 g/L and polyethylene glycol p-(1,1,3,3-tetramethylbutyl)-phenyl ether at a concentration in the buffer of 0.335 g/L.

2. The buffer of claim 1, wherein the optional at least one other nutrient consists of a nutrient broth at a concentration in the buffer of about 10 g/L to about 50 g/L.

3. The buffer of claim 1 wherein the buffer includes ammonium chloride and the concentration of ammonium chloride in the buffer is about 0.01 g/L to about 80 g/L.

4. The buffer of claim 1, wherein the optional at least one other nutrient consists of a nutrient broth consisting of: i) tryptone; ii) soy; iii) NaCl; iv) dipotassium phosphate ($K_2HPO_4$); and v) glucose.

5. The buffer of claim 1, wherein the buffer does not contain an antifoaming agent.

* * * * *